US011382514B1

United States Patent
Sughrue et al.

(10) Patent No.: US 11,382,514 B1
(45) Date of Patent: Jul. 12, 2022

(54) RELATIVE ACTIVATION SCORES FOR BRAIN PARCELS

(71) Applicant: Omniscient Neurotechnology Pty Limited, Sydney (AU)

(72) Inventors: Michael Edward Sughrue, Brighton le Sands (AU); Stephane Philippe Doyen, Mount Kuring Gai (AU); Peter James Nicholas, South Hurstville (AU); Xinling Jiang, Willoughby (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/521,687

(22) Filed: Nov. 8, 2021

(51) Int. Cl.
| | |
|---|---|
| *A61B 5/00* | (2006.01) |
| *G16H 50/30* | (2018.01) |
| *G16H 50/20* | (2018.01) |
| *A61B 5/055* | (2006.01) |
| *G01R 33/48* | (2006.01) |
| *G16H 20/70* | (2018.01) |

(52) U.S. Cl.
CPC ............ *A61B 5/0042* (2013.01); *A61B 5/055* (2013.01); *G01R 33/4806* (2013.01); *G16H 20/70* (2018.01); *G16H 50/20* (2018.01); *G16H 50/30* (2018.01); *A61B 2576/026* (2013.01)

(58) Field of Classification Search
CPC .............................. A61B 5/0042; G16H 50/30
See application file for complete search history.

(56) References Cited

U.S. PATENT DOCUMENTS

| 7,480,640 | B1 * | 1/2009 | Elad ........................ G06Q 10/10 706/14 |
| 9,519,981 | B2 * | 12/2016 | Sudarsky ............... G06T 11/206 |
| 11,188,850 | B2 * | 11/2021 | Pisner ................... G06F 9/4881 |

OTHER PUBLICATIONS

Doyen et al., "Hollow-tree Super: a directional and scalable approach for feature importance in boosted tree models," arXiv preprint arXiv:2104.03088, Apr. 2021, 28 pages.
Lundberg et al., "A Unified Approach to Interpreting Model Predictions," arXiv preprint arXiv: 1705.07874v2, May 2017, 10 pages.
Ribeiro et al., "'Why Should I Trust You?' Explaining the Predictions of Any Classifier," Proceedings of the 22nd ACM SIGKDD International Conference on Knowledge Discovery and Data Mining, Aug. 2016, pp. 1135-1144.

* cited by examiner

*Primary Examiner* — Joseph M Santos Rodriguez
(74) *Attorney, Agent, or Firm* — Fish & Richardson P.C.

(57) ABSTRACT

Methods, systems, and apparatus, including computer programs encoded on a computer storage medium, for generating explainability data that explains a medical condition in a subject. In one aspect, a method comprises: obtaining data identifying a plurality of brain parcels that are predicted to be relevant to the medical condition; receiving fMRI data for a brain of a subject; processing the fMRI data for the brain of the subject to determine a respective activation score for each of the plurality of brain parcels that are predicted to be relevant to the medical condition; determining, for each of the plurality of brain parcels that are predicted to be relevant to the medical condition, a relative activation score for the brain parcel; and taking an action based on the relative activation scores.

20 Claims, 10 Drawing Sheets

US 11,382,514 B1

RELATIVE ACTIVATION SCORES FOR BRAIN PARCELS

TECHNICAL FIELD

This specification relates to processing medical images.

BACKGROUND

Medical imaging includes techniques and processes for creating visual representations of an interior of a body for clinical analysis and medical intervention, as well as visual representation of physiology of some organs or tissues. Medical imaging can reveal internal structures hidden by skin and bones, and can be used to diagnose and treat various diseases. Medical imaging also can establish a database of normal anatomy and physiology to make it possible to identify abnormalities amongst cohorts. Some medical imaging can also provide insights into functional activity and structural connections of a brain.

SUMMARY

This specification generally describes technologies for processing medical images of brains and/or displaying the processed images in a user-interactive brain navigation system (e.g., interface). The disclosed technology can be used by clinicians and other medical professionals to glean insight about functional activity in a brain of a subject. Based on such insights, the clinicians and other medical professionals can perform improved and more informed diagnoses, treatments, operations, and/or research than with existing systems.

Throughout this specification, a "subject" can refer to, e.g., a patient, human, animal, or other specimen. A "population" of subjects can refer to a group of subjects.

A "parcel" in a brain refers to a region, e.g., a three-dimensional (3-D) volumetric region, of the brain. Typically, a parcel refers to region that has a specified function, structural connectivity, or cellular composition. A collection of parcels that collectively define a partition of the brain may be referred to as a "parcel atlas." A parcel atlas can include any appropriate number of parcels, e.g., 50 parcels, 100 parcels, 500 parcels, or 1000 parcels.

Generally, a parcel atlas can be chosen such that each parcel in the parcel atlas is expected to have broadly similar properties (e.g., functional activity, structural connectivity, or cellular composition) between subjects, even if the exact boundaries of the parcel differ between subjects. A parcel atlas can be a useful mechanism for analyzing brain images as it reduces the complexity of the brain architecture to a finite number of domains, which can be expected to play somewhat uniform roles in normal operation of the brain.

A brain can be imaged using a variety of possible imaging modalities. One such imaging modality is functional magnetic resonance imaging (fMRI). fMRI imaging of a brain over a sequence of time points yields a sequence of fMRI images, where each fMRI image corresponds to a respective time point and characterizes blood flow and/or blood oxygen level at each voxel in the brain at the time point. Blood flow/blood oxygen level in the brain is related to energy use by cells in the brain, and thus fMRI imaging provides a method of characterizing neural activity in the brain over time.

Parcel atlases can be particularly useful when analyzing fMRI data. For example, fMRI imaging of a brain of a subject over a sequence of time points can associate each voxel in the brain with a "blood flow curve." A blood flow curve associated with a voxel can characterize blood flow at location in the brain corresponding to the voxel at each time point in the sequence of time points. The respective blood flow curves corresponding to each voxel in a parcel can be averaged to generate an "average blood flow curve" for the parcel. A correlation between the respective average blood flow curves corresponding to two parcels in the brain can be understood to represent a measure of functional connectivity between the two parcels in the brain of the subject.

Throughout this specification, a "medical condition" in a subject can refer to a dysfunction or disorder in the subject. Examples of medical conditions can include, e.g., psychiatric conditions, e.g., schizophrenia, psychosis, or autism. In some cases, a medical condition can refer to a behavioral symptom, e.g., auditory hallucinations, visual hallucinations, or paranoia.

Particular embodiments of the subject matter described in this specification can be implemented so as to realize one or more of the following advantages.

This specification describes a parcel scoring system that can process fMRI data characterizing neural activity in the brain of a subject, e.g., a subject having a medical condition, to generate data, referred to as "explainability data," that "explains" the medical condition in the subject. That is, the explainability data can provide interpretable insight into the mechanism, cause, or state of the medical condition in the subject. In particular, the explainability data includes a set of "relative activation scores." Each relative activation score corresponds to a brain parcel and compares: (i) neural activity in the parcel in the brain of the subject, and (ii) a distribution of neural activity in the parcel across a population of subjects. The parcel scoring system can provide the explainability data to a user, e.g., by way of a user interface, for use by the user, e.g., in determining appropriate diagnoses, treatments, or surgical procedures to treat the medical condition in the subject.

The parcel scoring system increases the interpretive value of the relative activation scores by providing (e.g., to the user) relative activation scores for only a fraction of the parcels in a parcel atlas, in particular, for those parcels that are predicted to be relevant to the medical condition. Computing the relative activation scores for only the high-impact parcels significantly reduces the amount of data to be interpreted by a user. Interpreting the relative activation scores for hundreds or thousands of parcels in a full parcel atlas would be unmanageable for many users, and thus significantly detract from the interpretive value of the relative activation scores. Moreover, the high-impact parcels are precisely those parcels that are predicted to be relevant to the medical condition, and thus the relative activation scores for these parcels may provide the most interpretive value to the user in explaining the medical condition in the target subject.

The parcel scoring system can also enable more efficient use of computational resources (e.g., memory and computing power) by computing relative activation scores for only those parcels in the parcel atlas that are predicted to be relevant to the medical condition. To identify which parcels are relevant to the medical condition, the parcel scoring system can train a machine learning model to process fMRI data for an input patient to predict whether the input patient has the medical condition. After training the machine learning model, the parcel scoring system can determine a respective importance score for each parcel that measures the impact of the parcel on predictions generated by the machine learning model. The parcel scoring system can then use the importance scores to identify the parcels that are most relevant to the medical condition. The parcel scoring system can thus leverage the machine learning model to accurately identify parcels relevant to the medical condition.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a parcel scoring system that can process fMRI data characterizing neural activity in the brain of a subject, e.g., a subject having a medical condition, to generate explainability data that explains the medical condition in the subject. In particular, the explainability data compares, for each of multiple parcels that are predicted to be relevant to the medical condition: (i) neural activity in the parcel in the brain of the subject, and (ii) a distribution of neural activity in the parcel across a population of subjects. The explainability data can thus provide an interpretation for, e.g., which parcels in the brain of the subject are the greatest contributors to the medical condition in the subject. In the case of a subject that does not have the medical condition, the explainability data can provide an interpretation for, e.g., which parcels in the brain of the subject provide the most "protection" from the medical condition in the subject.

The parcel scoring system can provide the explainability data to a user, e.g., by way of a user interface on a user device. The user interface can enable the user to select one or more parcels in the brain of the subject, e.g., in response to viewing the explainability data. The parcel scoring system can perform a variety of possible actions in response to the selection, by the user, of one or more parcels in the brain of the subject. For example, the parcel scoring system can provide anatomical data representing the location of the selected parcels in a three-dimensional (3-D) model of the brain of the subject, e.g., by way of the user interface. As another example, the parcel scoring system can export data identifying the selected parcels, e.g., to a data store, or to another system, e.g., a system used to perform a medical procedure.

An example parcel scoring system will be described in more detail below with reference to FIG. 1.

The parcel scoring system can be implemented as part of a broader computer system that can optionally provide additional functionality and perform additional operations, e.g., involving processing medical images of brains and/or displaying the processed images.

An example computer system that can implement the parcel scoring system will be described in more detail below with reference to FIG. 7.

Figure 1:
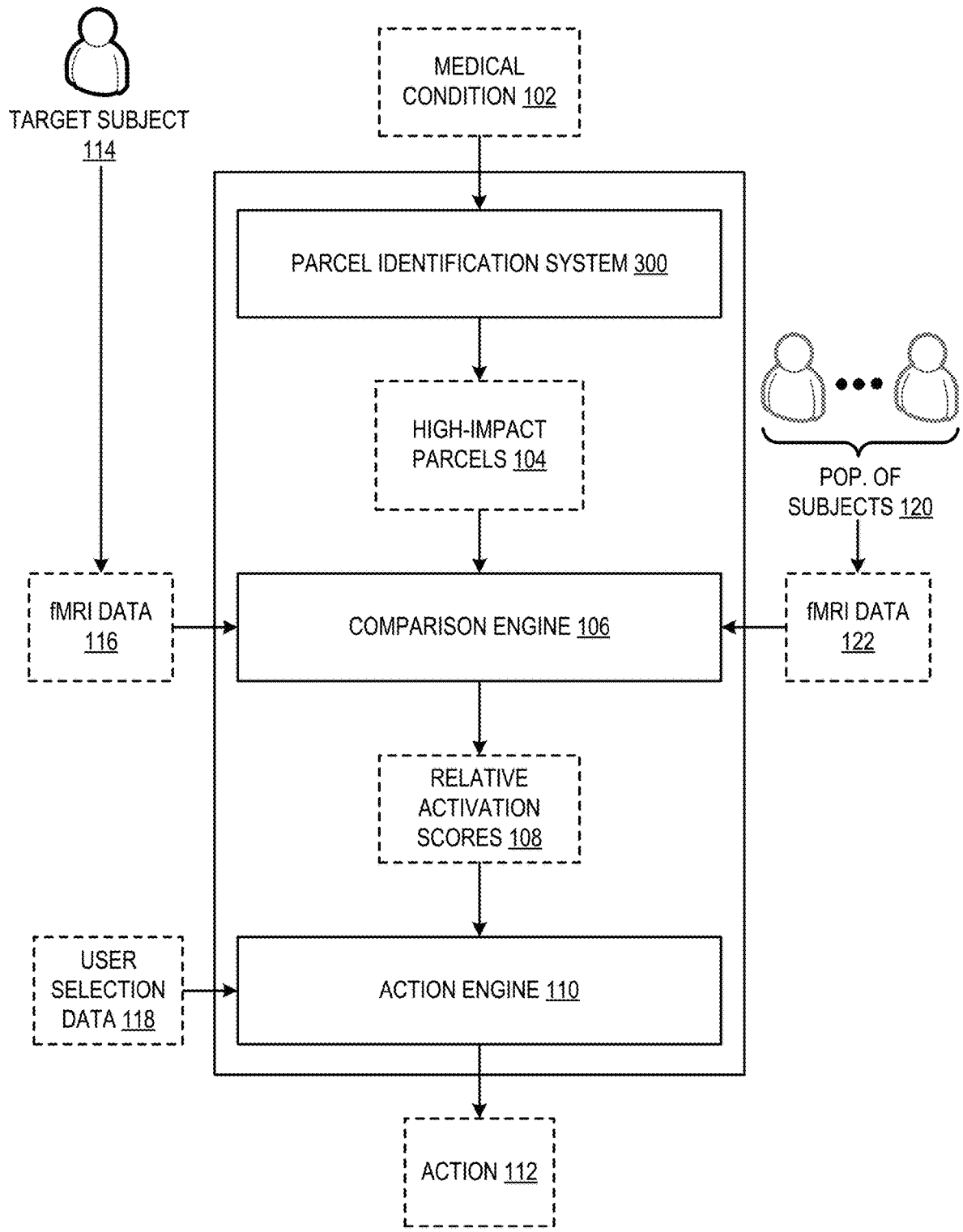
FIG. 1 shows an example parcel scoring system.

FIG. 1 shows an example parcel scoring system 100. The parcel scoring system 100 is an example of a system implemented as computer programs on one or more computers in one or more locations in which the systems, components, and techniques described below are implemented.

The parcel scoring system 100 is configured to receive, e.g., from a user by way of a user interface made available on a user device, a selection of a medical condition 102. The user can select the medical condition 102, e.g., from a predefined set of medical conditions.

The parcel scoring system 100 also receives fMRI data 116 characterizing the brain of a subject, referred to as the "target" subject 114. The parcel scoring system 100 can receive the fMRI data 116 for the target subject 114, e.g., directly from a medical imaging device (e.g., an fMRI imaging device) that generated the fMRI data 116, or by retrieving the fMRI data 116 from a data store. The target subject 114 may be a subject that is understood (e.g., by clinical diagnosis) as being likely to have the medical condition 102.

The parcel scoring system 100 includes a parcel identification system 300, a comparison engine 106, and an action engine 110, which are each described in more detail next.

The parcel identification system 300 is configured to identify a set of (multiple) "high-impact" (or "high contribution" or "high protection") brain parcels, from a parcel atlas, that are predicted to be relevant to the medical condition 102. A brain parcel may be relevant to the medical condition 102 (i.e., and thus designated as a "high-impact" parcel for the medical condition 102), e.g., if neural activity in the brain parcel is associated with the cause or mechanism of the medical condition in at least some subjects. For example, a high-impact parcel 104 may be part of a malfunctioning neural circuit that contributes to the medical condition 102 in the target subject 114.

Generally, the parcel identification system 300 designates only a fraction of the brain parcels in the parcel atlas as being high-impact brain parcels 104 for the medical condition 102. For example, the parcel identification system 300 can designate fewer than 50%, fewer than 20%, fewer than 10%, fewer than 5%, or fewer than 1% of the parcels in the parcel atlas as being high-impact parcels 104 for the medical condition 102. In other implementations, the parcel identification system can designate a fixed number (e.g., 5, 10 15, or 20) of high impact parcels.

The parcel identification system 300 can identify the set of high-impact parcels 104 for the medical condition 102 with reference to a machine learning model that is configured to process fMRI data characterizing a subject to predict whether the subject has the medical condition. In particular, the parcel identification system 300 can identify a set of parcels that have a significant impact on predictions generated by the machine learning model (i.e., for whether subjects have the medical condition), and thereafter designate the identified parcels as being high-impact parcels for the medical condition. Example operations that can be performed by the parcel identification system 300 to identify the set of high-impact parcels 104 for the medical condition 102 with reference to a machine learning model are described in more detail with reference to FIG. 3.

Generally, the set of high-impact parcels 104 associated with the medical condition 102 can be pre-computed. More specifically, the parcel identification system 300 is not required to re-compute the set of high-impact parcels 104 with reference to the machine learning model each time a user interacts with the parcel scoring system 100. Rather, the parcel identification system 300 can compute the high-impact parcels 104 for the medical condition with reference to the machine learning model once, and then store data identifying the high-impact parcels 104 for the medical condition 102 in a data store. Thereafter, in response to receiving a user input selecting a medical condition 102, the parcel identification system 300 can retrieve the high-impact parcels 104 for the selected medical condition 102 from the data store, rather than re-computing them.

The comparison engine 106 is configured to generate a score, referred to as "relative activation score" 108, for each high-impact parcel 104. Generally, the relative activation score 108 for a high-impact parcel 104 compares neural activity in the high-impact parcel 104 of the target subject 114 to a distribution of neural activity in the high-impact parcel 104 across a population of subjects 120. The relative activation scores 108 provide explainability data that contributes to explaining the medical condition 102 in the target subject 114, as will be described in more detail below.

To generate the relative activation score 108 for a high-impact parcel 104, the comparison engine 106 computes a respective "activation score" for the high-impact parcel 104 in: (i) the brain of the target subject, and (ii) the brain of each subject in a population of subjects 120. The population of subjects 120 can be, e.g., a population of subjects that have the medical condition 102, or a population of subjects that do not have the medical condition. (For convenience, the subjects in the population of subjects may be referred to herein as "reference" subjects).

The comparison engine 106 can generate the activation score for a parcel in a brain, based on fMRI data characterizing the parcel in the brain, in any of a variety of possible ways. For example, the comparison engine 106 can process fMRI data characterizing a parcel to determine the maximum value of the average blood flow curve for the parcel, and identify the maximum value of the average blood flow curve as the activation score for the parcel. As another example, the comparison engine 106 can process fMRI data characterizing a parcel to determine the average value of the average blood flow curve for the parcel, and identify the average value of the average blood flow curve for the parcel as the activation score for the parcel. As another example, the comparison engine 106 can process fMRI data characterizing a parcel to determine the median value of the average blood flow curve for the parcel, and identify the median value of the average blood flow curve for the parcel as the activation score for the parcel. As yet another example, the comparison engine 106 can process fMRI data characterizing a parcel to determine blood oxygen level or the comparison engine can process EEG data characterizing a parcel to determine electrical activity.

Thus, to generate the relative activation score 108 for a high-impact parcel 104, the comparison engine 106 processes fMRI data 116 for the target subject 114 to generate an activation score for the high-impact parcel 104 in the target subject 114. For each reference subject in the population of reference subjects 120, the comparison engine 106 processes fMRI data 122 for the reference subject 120 to generate an activation score for the high-impact parcel 104 in the reference subject. That is, the comparison engine 106 computes a distribution of activation scores for the high-impact parcel 104 across the population of reference subjects 120 (i.e., where the "distribution" includes the respective activation score for the high-impact parcel for each reference subject).

The comparison engine 106 generates the relative activation score 108 for each high-impact parcel 104 based on: (i) the activation score for the high-impact parcel 104 in the target subject 114, and (ii) the distribution of activation scores for the high-impact parcel 104 across the population of subjects 120. A few example techniques for generating the relative activation score 108 for a high-impact parcel 104 are described next.

In one example, the comparison engine 106 can generate the relative activation score 108 for a high-impact parcel 104 as a ratio of: (i) the activation score for the high-impact parcel 104 in the target subject 114, and (ii) the average activation score for the high-impact parcel 104 in the population of subjects 120.

Generally, the activation scores for each parcel in each subject in the population of reference subjects 120 can be pre-computed. More specifically, the comparison engine 106 is not required to re-compute the activation scores for the parcels of the reference subjects in the population of reference subjects 120 each time the comparison engine 106 generates relative activation scores 108 for a target subject 114. Rather, the comparison engine 106 can compute the activation scores for the parcels of the reference subjects once, and the store the activation scores in a data store. Thereafter, to compute the relative activation scores 108 for a target subject 114, the comparison engine 106 can retrieve the parcel activation scores for the population of reference subjects 120 from the data store, i.e., rather than re-computing them.

The relative activation scores 108 compare neural activity in the high-impact parcels 104 of the target subject 114 to the distribution of neural activity in the high-impact parcels 104 across the population of reference subjects 120. In doing so, the relative activation scores 108 provide explainability data that contributes to explaining the medical condition 102 in the target subject 114, e.g., by providing insight into the mechanism and cause of the medical condition 102 in the target subject 114. In particular, the relative activation scores 108 can provide insight into which parcels in the target subject 114 are likely to be significant contributors to the medical condition 102 experienced by the target subject 114.

For example, the relative activation score for a particular high-impact parcel may indicate that the activation score for the parcel in the target subject 114 differs significantly from the distribution of activation scores for the parcel across the population of subjects 120. In this example, a user may make an inference that neural activity in the parcel is a contributor to the medical condition 102 in the target subject 114.

By computing the relative activation scores 108 for only the fraction of the parcels in the parcel atlas that are predicted to be relevant to the medical condition (i.e., the high-impact parcels 104), the parcel scoring system 100 increases the interpretive value of the relative activation scores 108. First, computing the relative activation scores 108 for only the high-impact parcels 104 significantly reduces the amount of data to be interpreted by a user. Interpreting the relative activation scores for a hundred or more parcels in the full parcel atlas would be unmanageable for many users, and thus significantly detract from the interpretive value of the relative activation scores. Second, the high-impact parcels are precisely those parcels that are predicted to be relevant to the medical condition, and thus the relative activation scores 108 for these parcels may provide the most interpretive value to the user in explaining the medical condition in the target subject.

Figure 5:
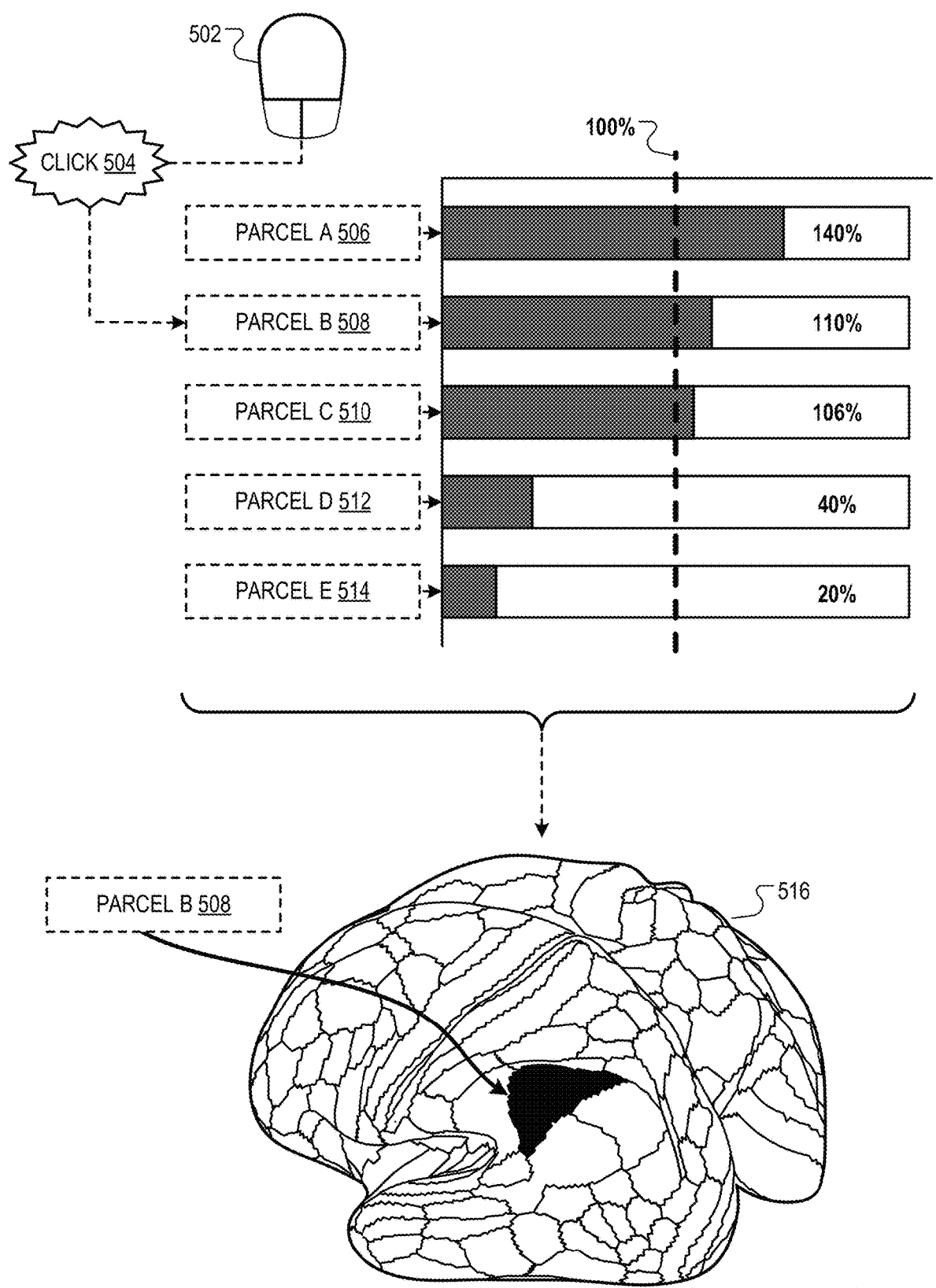
FIG. 5 illustrates an example of a user interface that graphically represents relative activation scores for high-impact parcels to a user, and enables the user to select a high-impact parcel to be displayed in a 3-D model of the brain of a target subject.

The action engine 110 is configured to provide the relative activation scores 108 to the user by way of the user interface on the user device. The relative activation scores 108 can be represented to the user on the user interface in any of a variety of possible ways. For example, the relative activation scores 108 can be presented to the user graphically, e.g., as a bar graph, where each bar in the bar graph corresponds to a respective high-impact parcel and the height of the bar represents the relative activation score 108 for the high-impact parcel. FIG. 5, which will be described in more detail below, illustrates an example of how the relative activation scores can be presented to a user.

The user interface on the user device can enable the user to select one or more of the high-impact parcels 104. For example, if the relative activation scores are presented to the user in the form of a bar graph (as described above), then the bars of the graph (and/or other elements of the user interface) may be selectable (i.e., interactive) elements. In this example, the user can select one or more high-impact parcels 104 by selecting interactive elements corresponding to those parcels in the user interface.

After receiving user selection data 118, i.e., that selects one or more of the high-impact parcels, the action engine 110 can perform any of a variety of possible actions based on the user selection data 118. A few examples of possible actions that can be performed by the action engine 110 in response to receiving the user selection data 118 are described next.

In one example, in response to receiving user selection data 118 that selects a parcel, the action engine 110 can obtain anatomical data that defines a volumetric region in the brain of the target subject 114 that corresponds to the selected parcel. The anatomical data for the selected parcel can be, e.g., data defining a polygonal mesh that encloses the volumetric region of the brain corresponding to the selected parcel in a 3-D model of the brain of the target subject 114. Anatomical data for the parcels in the brain of the target subject 114 can be pre-computed and stored in a data store, and the action engine 110 can obtain the anatomical data for the selected parcel by retrieving it from the data store.

After obtaining the anatomical data for the selected parcel, the action engine 110 can provide the anatomical data for display to the user by way of the user interface on the user device. The anatomical data for the selected parcel can be presented to the user in any of a variety of possible ways, e.g., as a polygonal mesh enclosing the volumetric region of the brain corresponding to the selected parcel in a 3-D model of the brain of the target subject.

In another example, to export a selected parcel, the action engine 110 can store data identifying the selected parcel in a data store.

Figure 2:
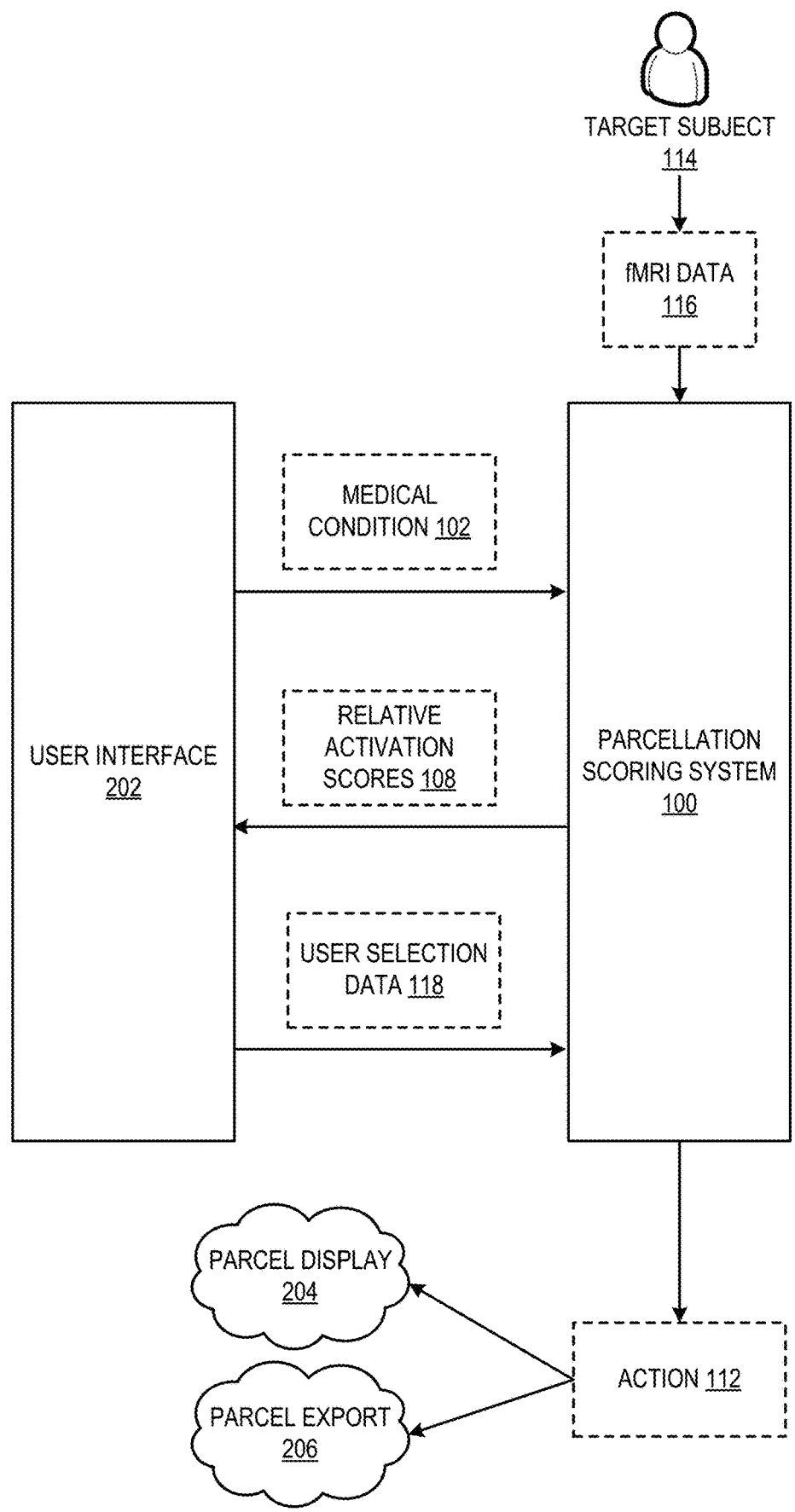
FIG. 2 illustrates a flow of data between a user interface and a parcel scoring system.

FIG. 2 illustrates a flow of data between: (i) a user interface 202, e.g., on a user device, and (ii) a parcel scoring system 100, e.g., as described with reference to FIG. 1.

The parcel scoring system 100 receives, by way of the user interface 202, a selection (e.g., by a user of the user device) of a medical condition 102, e.g., from a predefined set of medical conditions. The parcel scoring system 100 also receives fMRI data 116 for a target subject 114, e.g., a target subject 114 that has been diagnosed with the medical condition 102. The parcel scoring system 100 may receive the fMRI data 116 for the target subject 114 directly from a medical imaging device that captured the fMRI data 116, or the parcel scoring system 100 may retrieve the fMRI data 116 from a data store.

The parcel scoring system 100 identifies one or more high-impact parcels that are predicted to be relevant to the medical condition 102, and processes the fMRI data 116 for the target subject to generate a respective relative activation score 108 for each high-impact parcel 104. The relative activation score 108 for a high-impact parcel compares neural activity in the high-impact parcel of the target subject 114 to the distribution of neural activity in the high-impact parcel 104 across a population of subjects, e.g., a population of subjects that have the medical condition 102. The relative activation scores 108 provide explainability data that can contribute to explaining the medical condition 102 in the target subject 114, e.g., by providing insight into the mechanism and cause of the medical condition 102 in the target subject 114.

After generating the relative activation scores 108, the parcel scoring system 100 provides the relative activation scores 108 for display on the user interface 202. The relative activation scores 108 can be represented to the user by the user interface 202 in any of a variety of possible ways, e.g., graphically, as a bar graph, as illustrated with reference to FIG. 5.

After the relative activation scores 108 are presented to the user on the user interface 202, the user can interact with the user interface 202 to select one or more of the high-impact parcels. The user selection data 118, i.e., identifying the high-impact parcels selected by the user, is provided to the parcel scoring system 100.

In response to receiving the user selection data 118 that selects one or more of the high-impact parcels, the parcel scoring system 100 can perform a variety of possible actions 112. For example, the parcel scoring system 100 can obtain anatomical data defining the locations of the selected parcels in the brain of the target subject 114, and provide a visual representation 204 of the selected parcels to the user by way of the user interface, e.g., as illustrated with reference to FIG. 5. As another example, the parcel scoring system 100 can export 206 the selected parcels, e.g., by storing data identifying the selected parcels in a data store.

Figure 3:
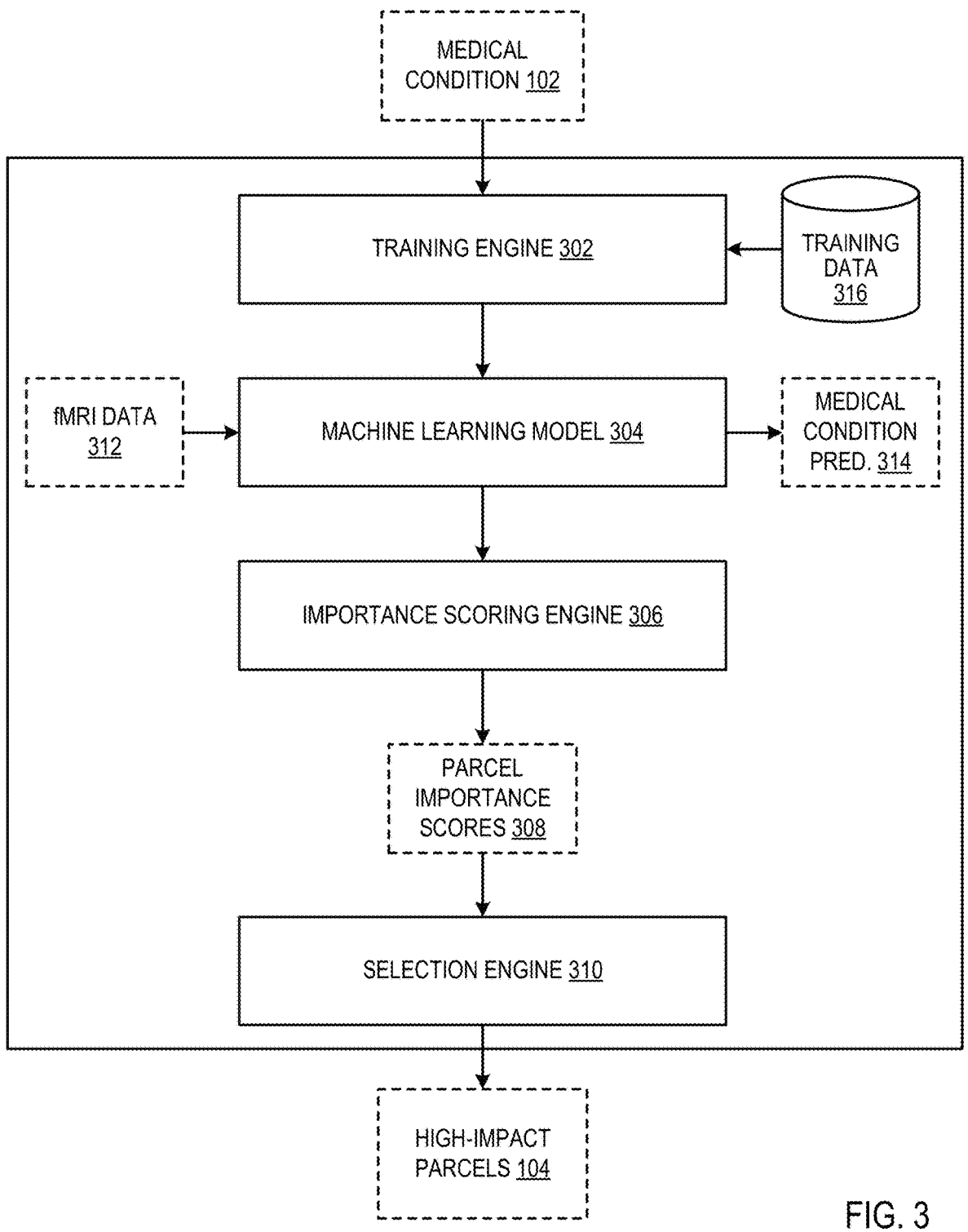
FIG. 3 shows an example parcel identification system.

FIG. 3 shows an example parcel identification system 300. The parcel identification system 300 is an example of a system implemented as computer programs on one or more computers in one or more locations in which the systems, components, and techniques described below are implemented.

The parcel identification system 300 is configured to receive data identifying a medical condition 102, and to generate data identifying one or more parcels from a parcel atlas as being "high-impact" parcels, i.e., parcels that are predicted to be relevant to the medical condition 102 or parcels that have the most different activity (high or low) in subjects with the condition relative to subjects without the condition.

The parcel identification system 300 identifies the high-impact parcels using a training engine 302, a machine learning model 304, an importance scoring engine 306, and a selection engine 310, which are each described in more detail next.

The training engine 302 is configured to train the machine learning model 304 on a set of training data 316.

The machine learning model 304 is configured to process fMRI data 312 characterizing the brain of a subject to generate a prediction 314 for whether the subject has the medical condition 102.

The fMRI data 312 processed by the machine learning model 304 can be represented in a variety of possible ways, i.e., prior to being provided for processing by the machine learning model 304. For example, the fMRI data 312 can be represented as a "functional connectivity matrix" having a number of rows and columns equal to the number of parcels in the parcel atlas. The value at position j) in the functional connectivity matrix can be defined as a correlation between the activity, e.g., the average blood flow curves, corresponding to parcel i and parcel j in the brain of the subject. As another example, the fMRI data 312 can be represented as a "functional connectivity vector" having a number of entries equal the number of parcels in the parcel atlas. Each entry in the functional connectivity vector can be obtained by combining, e.g., summing or averaging, a corresponding row or column of the functional connectivity matrix.

The prediction 314 generated by the machine learning model 304 can define a predicted likelihood that the subject has the medical condition. In particular, the prediction 314 can be a numerical value, e.g., in the range [0,1], that defines a predicted likelihood of the subject having the medical condition.

The machine learning model 304 can be any model having a set of learnable parameters that can be trained to perform a prediction task. For example, the machine learning model can include, e.g., a neural network model, a random forest model, a support vector machine model, a boosted decision tree, or a combination thereof.

The training data 316 includes multiple training examples, where each training example corresponds to a respective subject and includes: (i) fMRI data characterizing the brain of the subject, and (ii) a target output that identifies whether the subject has the medical condition 102. The training data 316 can include any appropriate number of training examples, e.g., 100 training examples, 1000 training examples, or 10,000 training examples. The training data 316 includes at least some training examples corresponding to subjects that have the medical condition 102, and at least some training examples corresponding to subjects that do not have the medical condition 102.

Generally, for each training example in the training data 316, the training engine 302 trains the machine learning model 304 to process the fMRI data included in the training example to generate a prediction that matches the target output specified by the training example.

The training engine 302 can train the machine learning model 304 on the training data 316 using any appropriate training technique. For example, if the machine learning model 304 is a neural network model, then the training engine 302 can train the machine learning model 304 using a stochastic gradient descent training technique.

The importance scoring engine 306 is configured to generate a respective importance score 308 for each parcel in the parcel atlas, where the importance score 308 for a parcel measures the impact of the parcel on predictions generated by the (trained) machine learning model 304. The impact of a parcel on predictions generated by the machine learning model 304 can refer to, e.g., a scale of the change in predictions generated by the machine learning model 304 that would result from modifying the portion of the fMRI data characterizing neural activity in the parcel.

The importance scoring engine 306 can generate the importance scores 308 for the parcels in the parcel atlas using any appropriate technique. Example techniques for generating the importance scores are described with reference to: S. Doyen et al., "Hollow-tree Super: a directional and scalable approach for feature importance in boosted tree models," arXiv:2104.03088 (2021); S. M. Lundberg et al., "A unified approach to interpreting model predictions," arXiv:1705.07874v2 (2017); M. T. Ribeiro et al., "Why should I trust you: explaining the prediction of any classifier," Proceedings of the $22^{nd}$ ACM SIGKDD International Conference on Knowledge Discovery and Data Mining, pp. 1135-1144 (2016).

Figure 4:
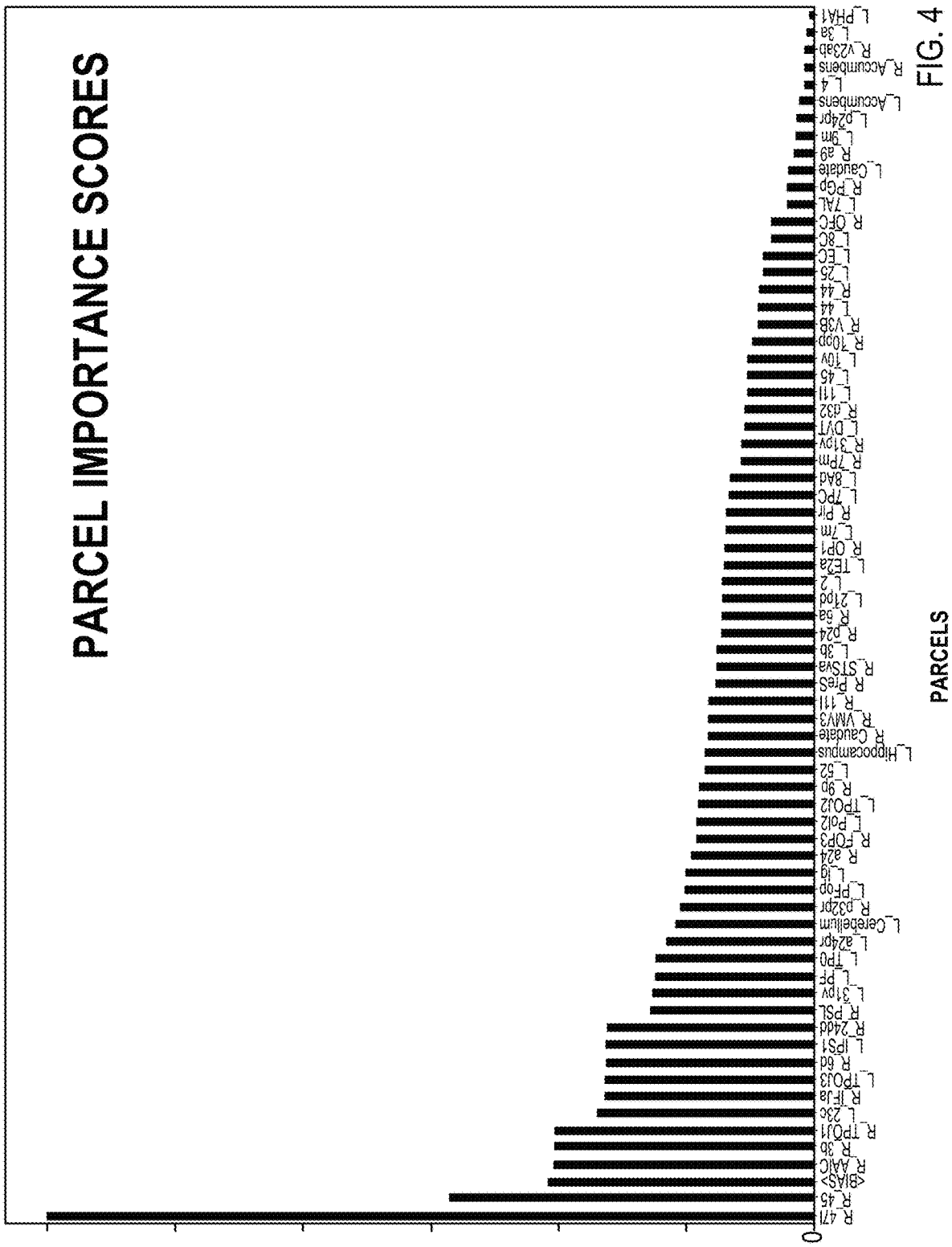
FIG. 4 illustrates an example distribution of importance scores for a set of parcels.

Generally, the importance score for a parcel can be understood as being proportionate to the relevance of the parcel to the medical condition. That is, a parcel associated with a higher importance score can be understood as being more relevant to the medical condition, e.g., because neural activity in that parcel has a higher impact on predictions, generated by the machine learning, for whether subjects have the medical condition. FIG. 4 illustrates an example distribution of importance scores for a set of parcels.

The selection engine 310 is configured to receive the importance scores 308 for the parcels, and to designate a proper subset of the parcels in the parcel atlas as being high-impact parcels 104 based on the importance scores 308.

The selection engine 310 can select the high-impact parcels 104 from the parcel atlas based on the importance scores 308 of the parcels in the parcel atlas in any of a variety of ways. For example, the selection engine 310 can designate any parcel having an importance score 308 that satisfies (e.g., exceeds) a predefined threshold value as being a high-impact parcel 104. As another example, the selection engine 310 can designate a predefined number of parcels having the highest importance scores 308 as being high-impact parcels 104.

After determining the high-impact parcels 104 for the medical condition 102, the parcel identification system 300 can provide data identifying the high-impact parcels 104 for the medical condition 102, e.g., to the parcel scoring system described with reference to FIG. 1.

The parcel identification system 300 can determine high-impact parcels 104 for a variety of medical conditions using the techniques described above. The set of high-impact parcels for one medical condition will typically be different than the set of high-impact parcels for another medical condition, reflecting the diversity in underlying causes and mechanisms of medical conditions affecting the brain.

FIG. 4 illustrates an example distribution of importance scores for a set of parcels. In particular, for each parcel identified on the horizontal axis, the height of the corresponding bar represents an importance score for the parcel that measures an impact of the parcel of predictions generated by the machine learning model for whether subjects have a particular medical condition. It can be appreciated that the magnitude of the importance scores vary widely across the set of parcels. The parcel scoring system (described with reference to FIG. 1) computes relative activation scores (i.e., that compare neural activity between a target subject and a population of subjects) for only a proper subset of the parcels in a parcel atlas, e.g., for the parcels having the highest importance scores. The parcel scoring system thus increases the interpretability of the relative activation scores and their relevance to explaining a medical condition in the target subject.

FIG. 5 illustrates an example of a user interface that graphically represents relative activation scores for high-impact parcels to a user, and enables the user to select a high-impact parcel to be displayed in a 3-D model of the brain of a target subject.

In particular, the user interface displays the relative activation scores for five high-impact parcels, i.e., parcel A 506, parcel B 508, parcel C 510, parcel D 512, and parcel E 514, in the brain of the target subject. The relative activation score for each high-impact parcel is represented by the length of a bar in a bar graph, and also as a percentage. For example, the user interface indicates that the relative activation score for parcel A is 140%, while the relative activation score for parcel E is 20%.

The user interface enables a user to interact with the user interface to select a high-impact parcel, e.g., the user can use a mouse 502 (or another input device) to click 504 (or otherwise interact) with the representation of parcel B 508 on the user interface.

In response to the user selecting a high-impact parcel, the user interface can display a 3-D model of the brain of the target patient that illustrates the spatial location of the selected high-impact parcel in the brain of the brain target patient. For example, in response to the user selecting parcel B 508, the user interface can display the 3-D model 516 of the brain of the target patient that visually highlights the spatial location of parcel B 508.

Figure 6:
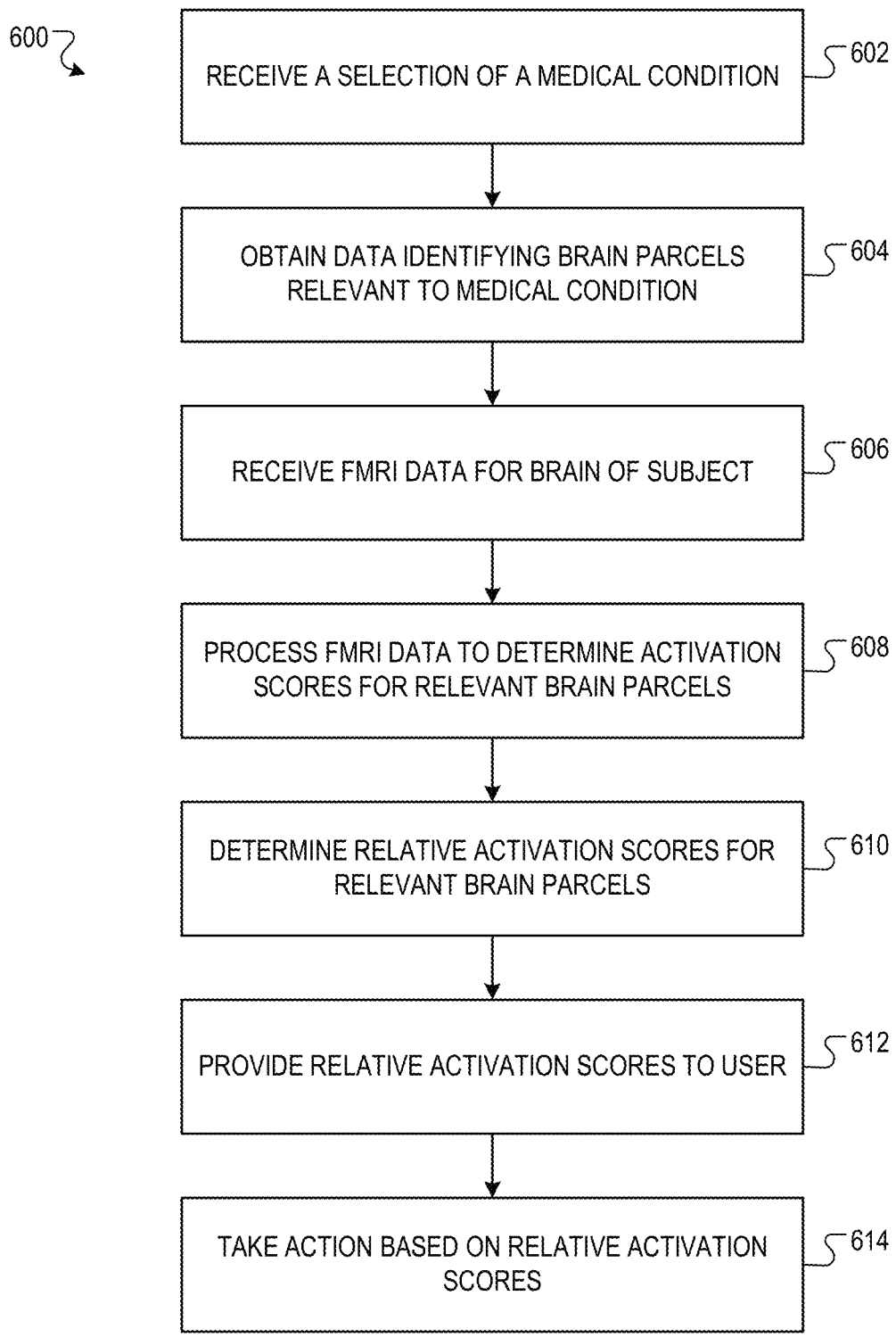
FIG. 6 is a flow diagram of an example process for providing, to a user, a respective relative activation score for each brain parcel in a set of brain parcels that are predicted to be relevant to a medical condition.

FIG. 6 is a flow diagram of an example process 600 for providing, to a user, a respective relative activation score for each brain parcel in a set of brain parcels that are predicted to be relevant to a medical condition. For convenience, the process 600 will be described as being performed by a system of one or more computers located in one or more locations. For example, a parcel scoring system, e.g., the parcel scoring system 100 of FIG. 1, appropriately programmed in accordance with this specification, can perform the process 600.

The system receives a selection of a medical condition (602). The user can select the medical condition, e.g., from a predefined set of medical conditions.

The system obtains data identifying a set of brain parcels that are predicted to be relevant to the medical condition (604). The system may have previously identified the set of brain parcels that are predicted to be relevant to the medical condition by training a machine learning model to process an input derived from fMRI data for a brain of an input subject to predict whether the input subject has the medical condition. The system may then have identified the set of brain parcels that are predicted to be relevant to the medical condition using the machine learning model.

The system receives fMRI data for a brain of a subject (606). For example, the system can retrieve the fMRI data for the brain of the subject from a data store.

The system processes the fMRI data for the brain of the subject to determine a respective activation score for each of the brain parcels that are predicted to be relevant to the medical condition (608). The activation score for a brain parcel can characterize neural activity in the brain parcel.

The system determines, for each of the brain parcels that are predicted to be relevant to the medical condition, a relative activation score for the brain parcel based on: (i) the activation score for the brain parcel in the subject, and (ii) a distribution of activation scores for the brain parcel across a population of subjects (610). For example, the system can determine the relative activation score for a brain parcel based on a ratio of: (i) the activation score for the brain parcel in the subject, and (ii) a measure of central tendency of the distribution of activation scores for the brain parcel across the population of subjects.

The system provides, to a user device of a user, the relative activation scores for the brain parcels that are predicted to be relevant to the medical condition as explainability data that explains the medical condition in the subject (612).

The system takes an action based on the relative activation scores (614). For example, after providing the relative activation scores to the user device of the user, the system can receive selection data from the user that selects one or more of the brain parcels that are predicted to be relevant to the medical condition. The system can then take one or more actions in response to receiving the selection data from the user, e.g., displaying anatomical data identifying the locations of the selected parcels in a 3-D model of the brain of the subject.

Figure 7:
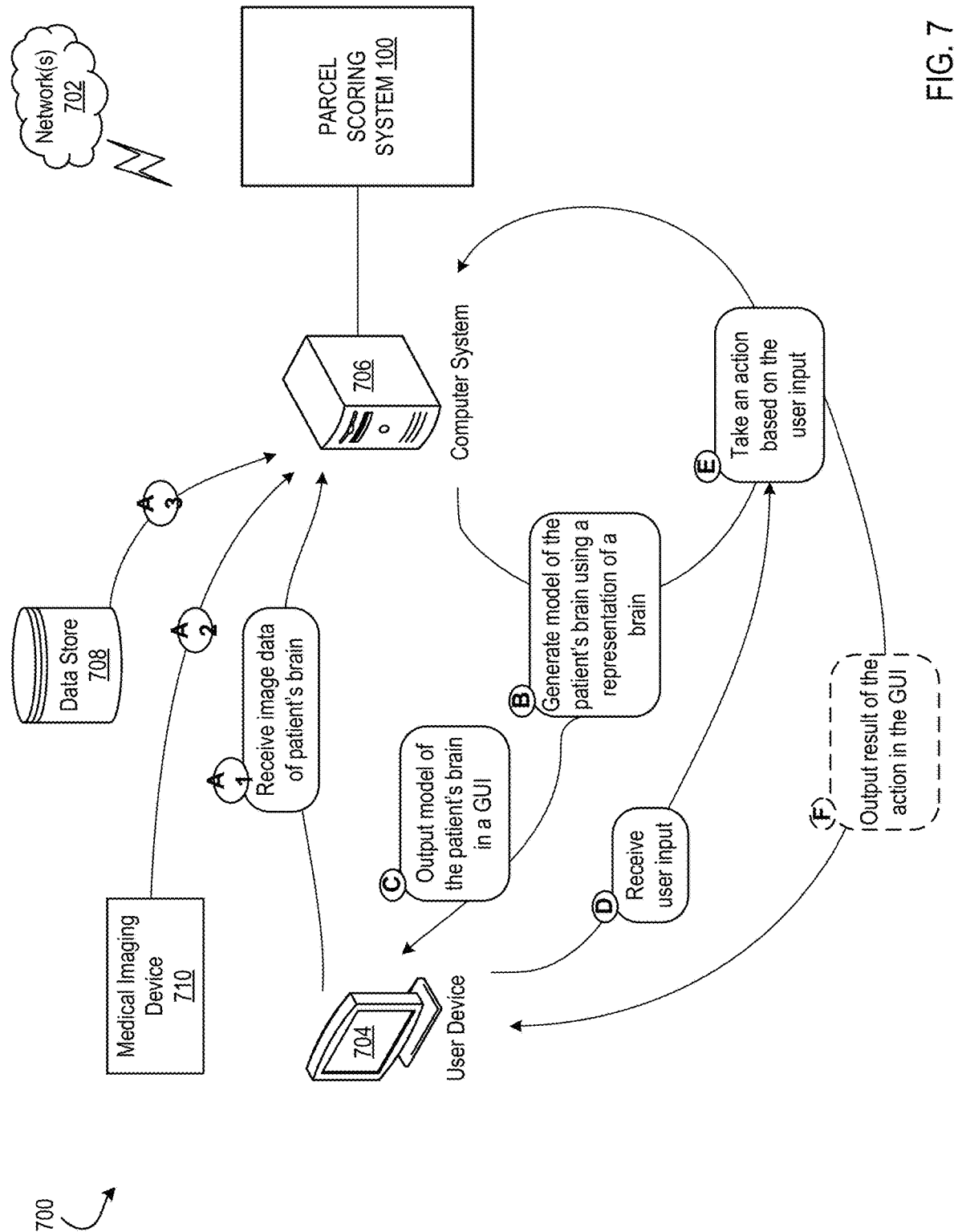
FIG. 7 is a conceptual diagram illustrating a computing environment for generating a graphical user interface (GUI) representation of a particular brain.

FIG. 7 is a conceptual diagram illustrating a computing environment 700 for generating a GUI representation of a particular brain. The computing environment 700 can include a user device 704, a computer system 706, a data store 708, and a medical imaging device 710, which can communicate (e.g., wired and/or wirelessly) via network(s) 702.

The user device 704 can be used by a medical professional, such as a clinician, surgeon, doctor, nurse, researcher, or other professional. The user device 704 and technologies described herein can be used by any other user. The user device 704 can be any one of a computer, laptop, tablet, mobile device, mobile phone, and/or smartphone. Sometimes, the user device 704 can be integrated into or otherwise part of one or more other devices in a medical setting, such as the medical imaging device 710 and/or the computer system 706. The medical professional can use the user device 704 to view information about a patient's brain. For example, using the disclosed technology, the medical professional can view, at the user device 704, 3D representations of a particular patient's brain and make determinations about what diagnosis, treatment, and/or surgical procedures to perform. The medical professional can also view other/additional information about the particular patient at the user device 704 to make more informed decisions with regards to the particular patient's diagnosis, treatment, surgery, or other medical or research purposes. Thus, the user device 704 can provide hardware that can support the GUIs, software, and applications described herein, such as a singular and interactive brain navigation system that makes it easier and more intuitive for the medical professionals to make medical and research determinations.

The computer system 706 can be a remote computing system, a cloud-based system or service, and/or integrated with or otherwise part of one or more devices in a medical setting (e.g., such as the user device 704 and/or the medical imaging device 710). The computer system 706 can be a computer, processor, a network of computers, a server, and/or a network of servers. Sometimes, each medical setting (e.g. a hospital) can have one or more computer systems 706. Sometimes, the computer system 706 can be used across multiple medical settings (e.g., multiple hospitals). The computer system 706 can be configured to generate interactive representations of patients' brains based off image data of the brains. The computer system 706 can also generate GUIs to display the interactive representations of the brains at the user device 704.

Sometimes, the computer system 706 can clean the image data by removing personally identifying information (e.g., protected health information (PHI)) from that data. Cleaning the image data can be beneficial to preserve patient privacy, especially if the interactive representations of patients' brains are used for medical research, clinical studies, or otherwise are stored in the data store 708 for future retrieval and use. Removing personally identifying information can also be advantageous if the computer system 706 is remote from the user device 704 and the interactive representations of the brain are generated at the computer system 706 that is outside a secure hospital infrastructure or other network where the image data may be generated and/or the interactive representations of the brain may be outputted. In other words, removing personally identifying information can be advantageous to preserve patient privacy when patient data is communicated between different networks and/or infrastructure.

The computer system 706 can implement the parcel scoring system 100 described with reference to FIG. 1. The computer system 706 can implement the operations of the parcel scoring system 100, as an alternative to or in combination with the other operations described with reference to FIG. 7.

The data store 708 can be a remote data store, cloud-based, or integrated into or otherwise part of one or more other components in the medical setting (e.g., such as the user device 704 and/or the computer system 706). The data store 708 can store different types of information, including but not limited to image data of patient brains (e.g., from the medical imaging device 710), cleaned image data (e.g., from the computer system 706), 3D representations of patient brains or other interactive representations of patient brains (e.g., from the computer system 706), connectivity data associated with patient brains, determinations, actions, or other user input taken by the medical professional (e.g., at the user device 704), patient information or records, or other relevant information that can be used in a medical setting.

The medical imaging device 710 can be any type of device and/or system that is used in the medical setting to capture image data of patient brains. The medical imaging device 710 can capture image data that includes but is not limited to x-rays, computed tomography (CT) scans, magnetic resonance imaging (Mills), electroencephalography (EEG) and/or ultrasound. One or more other types of image data can also be captured by the medical imaging device 710. The computer system 706 can be configured to receive any type of image data of a patient's brain and glean connectivity data about the brain from that image data to map the data onto a user-friendly interactive representation of a brain.

Still referring to FIG. 1, the computer system 706 can receive image data of a patient's brain from one or more of the user device 704 (step A1), the medical imaging device 710 (step A2), and the data store 708 (step A3). Sometimes, for example, when the user device 704 is part of the medical imaging device 710, the computer system can receive the image data captured by the medical imaging device 710 from only one device (e.g., the medical imaging device 710 or the user device 704). The image data can be captured by the medical imaging device 710 then sent directly, in real-time, to the computer system 706 (step A2) for real-time processing. Sometimes, the image data can be captured by the medical imaging device 710, then initially reviewed by the medical professional at the user device 704. Accordingly, the user device 704 can transmit the image data to the computer system 706 (step A1).

In some implementations, image data can be captured of multiple different brains by multiple different medical imaging devices 710. The image data can be stored in the data store 708 for future processing and analysis. The computer system 706 can then retrieve a batch or batches of the image data from the data store 708 (step A3) and process the image data in batch. Processing in batch can be advantageous to use fewer computational resources and reduce network bandwidth.

Once the computer system 706 receives the image data (steps A1-A3), the computer system can generate a model of the brain using a representation of a brain (step B). For example, the computer system 706 can map or model the patient's brain from the image data onto a 3D representation of a brain. The 3D representation can be a generic brain in 3-dimensional or other multi-dimensional space. The 3D representation can be a glass brain. Mapping the patient's brain onto the glass brain can be advantageous to provide vantage points of different structures, parcels, and connectivity in the particular patient's brain. A medical professional can more easily analyze the particular patient's brain via the 3D representation of the brain rather than through the raw image data captured by the medical imaging device 710. As a result, the medical professional can generate more informed decisions and determinations with regards to the particular patient's diagnosis, treatment, surgery, condition, or other medical or research purposes.

Once the patient's brain is modeled using the representation of the brain (step B), the computer system 706 can output the model of the patient's brain in a GUI at the user device 704 (step C). For example, the computer system 706 can generate the GUI that displays the model of the patient's brain, then transmit the GUI to the user device 704 to be outputted. The model can represent the patient's brain overlaid on the glass brain. Sometimes, instead of outputting the model at the user device 704 (step C), the computer system 706 can store the model of the patient's brain in the data store 708. The model of the patient's brain can then be accessed/retrieved at a later time and presented to the medical professional or other user at the user device 704.

As mentioned throughout, when the model of the patient's brain is outputted at the user device 704, the GUI can allow the user, e.g., a medical professional, to take numerous actions in response to reviewing the model of the patient's brain. For example, the medical professional can determine what type of diagnosis, treatment, or surgical procedures to take with regards to this particular patient. The medical professional can also interact with the model of the patient's brain through use-selectable options and features in the GUI that is outputted at the user device 704. The medical professional can change views of the model of the patient's brain (e.g., rotate around the model, view only a left or right side of the patient's brain, etc.), select portions of the patient's brain from the model (e.g., select a particular lobe, node, parcel, etc.), view other information about the patient (e.g., health records, prior medical visits, etc.), and simulate surgical procedures that can impact different parcels or portions of the patient's brain (e.g., slicing a node or nodes that are connected to other nodes in the patient's brain). The medical professional can provide input to the user device 704, for example, via an input device, and the input can indicate the medical professional's interaction(s) with the model of the patient's brain. This input can then be received by the computer system 706 (step D).

The computer system 706 can take an action based on the received user input (step E). For example, if the medical professional changes or selects a different view of the model of the patient's brain, then the computer system 706 can generate an updated GUI display of the patient's brain that only includes the selected view. This updated GUI display can be outputted at the user device (step F). As another example, the medical professional can remove one or more nodes from the model of the patient's brain. The computer system 706 can receive this input (step D), simulate removal of the user-selected nodes (step E), then output results of removing such nodes from the brain at the user device 704 (step F). The medical professional can review the outputted results and take further actions in response. Further actions can include decisions about what nodes the medical professional should remove during the actual medical procedure and/or how to proceed with diagnosis, treatment, and/or the medical procedure.

Sometimes, the computer system 706 can take an action based on the user input (step E) that does not also include outputting a result of the action at the user device 704 (step F). For example, the medical professional can input notes about what actions the medical professional intends to take during a medical procedure, a diagnosis for the particular patient, and/or treatment for the patient. The computer system 706 can receive this input and store it in the data store 708 but may not output results from storing this input. This input can then be retrieved from the data store 708 and provided to one or more other devices (e.g., a report can be generated that indicates the patient's diagnosis and treatment). The report can then be provided to a device of the patient. The report can also be transmitted to devices of other medical professionals, such as those in a hospital infrastructure/network). The computer system 706 can take one or more other actions based on the user input (step E) and optionally output results of the action(s) at the user device 704 (step F).

Figure 8:
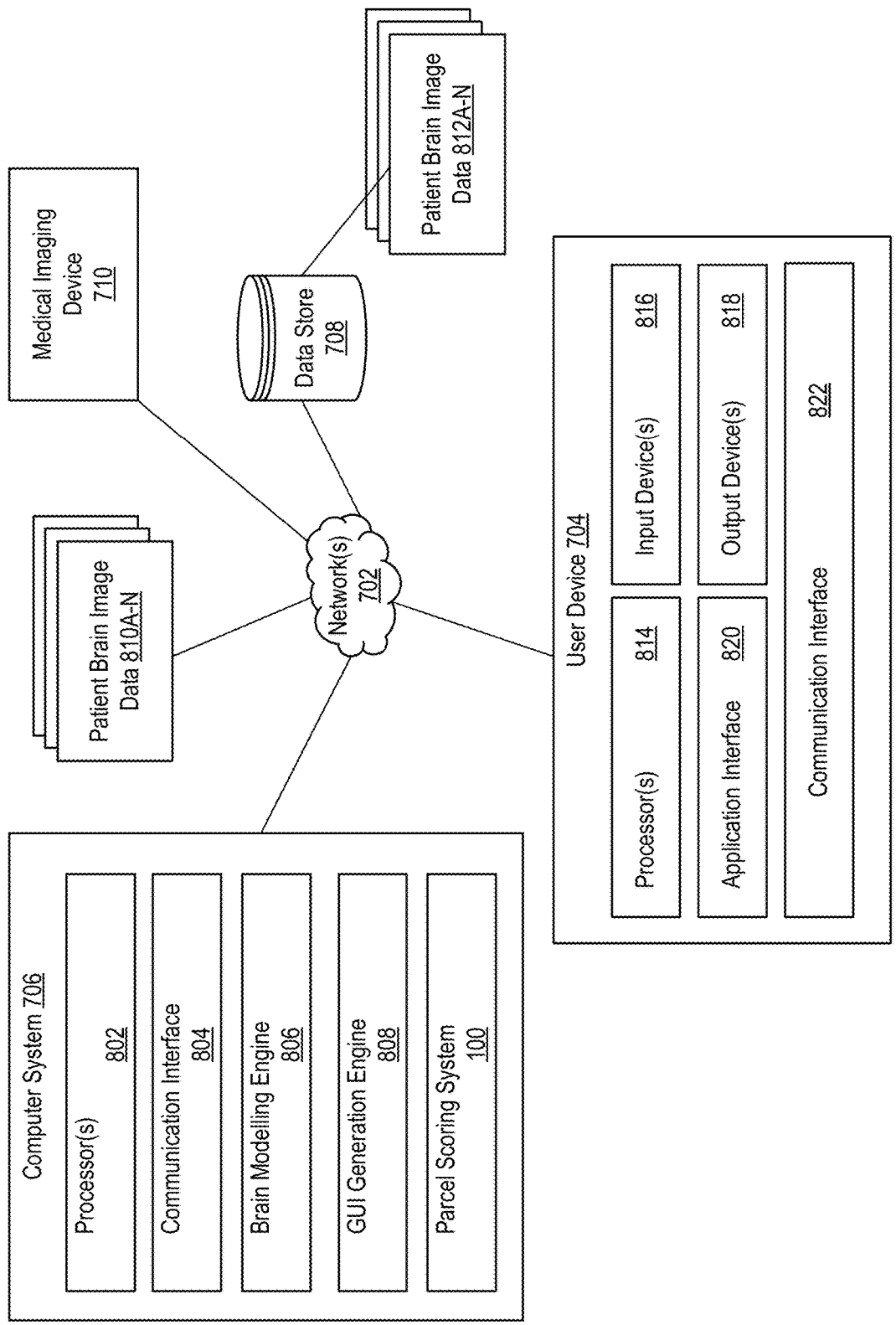
FIG. 8 illustrates components in a computing landscape that can be used to generate the GUI representation of the particular brain.

FIG. 8 illustrates components in a computing landscape that can be used to generate the GUI representation of the particular brain. As described above, the user device 104, computer system 706, data store 708, and medical imaging device 710 can communicate via the network(s) 102. One or more of the components 104, 706, 708, and 710 can also be integrated into a same computing system, network of devices, server, cloud-based service, etc. The network(s) 102 may be a wide-area network (WAN), such as the Internet, a cellular telecommunications network, or a private WAN. Connection via the network(s) 102 can include a traditional dial-up modem, a high-capacity (e.g., cable) connection such as a broadband modem, and/or a wireless modem.

The computer system 706 can include processor(s) 802, communication interface 804, brain modelling engine 806, GUI generation engine 808, and the parcel scoring system 100 described with reference to FIG. 1. The processor(s) 802 can be configured to perform one or more operations described herein. Although not depicted, the computer system 706 can also include at least one memory unit, which may have semiconductor random access memory (RAM) and semiconductor read only memory (ROM).

One or more of the techniques and processes described herein can be implemented as software application programs executable by the processor(s) 802 in the computer system 706. Moreover, one or more of the techniques and processes described herein can be executed in browsers at remote terminals, systems, or devices (e.g., the user device 104 and/or another computer system), thereby enabling a user of the remote terminals, systems, or devices to access the software application programs that are executing on the computer system 706. For example, steps for any of the techniques and processes described herein can be effected by instructions in the software application programs that are carried out within the computer system 706. Software instructions may be formed as one or more code modules (e.g., using PYTHON or equivalent language modules installed on the computer system 706 and/or the remote terminals, systems, or devices), each for performing one or more particular tasks. The software instructions can also be divided into separate parts. For example, a first part and the corresponding code module(s) can perform the techniques and processes described herein and a second part and the corresponding code module(s) can manage a user interface (e.g., the GUIs described herein) between the first part and the medical professional at the user device 104.

Moreover, the software may be stored in a non-transitory, tangible, computer readable medium, including storage devices described throughout this disclosure. The software can be loaded into the computer system 706 from the computer readable medium, and then executed by the computer system 706. A computer readable medium having such software or computer program recorded on the computer readable medium can be a computer program product. Examples of transitory or non-tangible computer readable transmission media that may also participate in the provision of software, application programs, instructions and/or data include radio or infra-red transmission channels as well as a network connection to another computer or networked device, and the Internet or Intranets, including e-mail transmissions and information recorded on Websites and the like.

Still referring to the computer system 706, the brain modelling engine 806 can be configured to map a patient's brain onto a representation of a brain (e.g., refer to step B in FIG. 1). For example, the brain modelling engine 806 can receive patient brain image data 810A-N, which can be used to generate a model of the patient's brain. The patient brain image data 810A-N can be received from the medical imaging device 710. The patient brain image data 810A-N can also be received from the user device 104. In some implementations, as described in reference to FIG. 1, the computer system 706 can retrieve patient brain image data 812A-N from the data store 708. The patient brain image data 812A-N can then be used by the brain modelling engine 806 to model the patient's brain.

Sometimes, modelling the brain can include identifying connectivity data for the particular brain. Modelling the brain can then include mapping the connectivity data over the representation of a generic brain. In yet some implementations, modelling the patient's brain can include identifying hubs, parcels, deep nodes, lateral nodes, and other portions of the patient's brain that can be mapped onto the representation of the generic brain. Moreover, the brain modelling engine 806 can be configured to identify personally identifying information in the image data of the brain and extract that information before mapping the patient's brain onto the representation of the generic brain. The brain modelling engine 806 can use one or more machine learning models to accurately map the particular patient's brain data onto a representation of the generic brain.

In some implementations, for example, Digital Imaging and Communications in Medicine (DICOM) images of a particular brain to be parcellated can be processed by the brain modelling engine 806. DICOM is an international standard for transmitting, storing, retrieving, processing and/or displaying medical imaging information. A registration function for the particular brain can be determined in a Montreal Neurological Institute (MNI) space (a common coordinate space) described by a set of standard brain data image sets, a registered atlas from a human connectome project can be determined, and diffusion tractography of the DICOM images can be performed to determine a set of whole brain tractography images of the particular brain (in neuroscience, tractography can be thought of as a 3D modelling technique used to represent white matter tracts visually). For each voxel in a particular parcel in the registered atlas, voxel level tractography vectors showing connectivity of the voxel with voxels in other parcels can be determined, the voxel can be classified based on the probability of the voxel being part of the particular parcel, and determining of the voxel level tractography vectors and the classifying of the voxels for all parcels of the HCP-MMP1 Atlas can be repeated to form a personalised brain atlas (PBs Atlas) containing an adjusted parcel scheme reflecting the particular brain.

The GUI generation engine 808 can be configured to generate GUI displays of the modelled brain. The GUI generation engine 808 can receive the modelled brain from the brain modelling engine 806 and generate an appropriate GUI for displaying the modelled brain to the medical professional (e.g., refer to FIG. 3). The GUI generation engine 808 can also transmit the generated GUI(s) to the user device 104 to be outputted/presented to the medical professional.

Moreover, whenever user input is received from the user device 104 that includes performing some action in response to the outputted model of the brain, the input can be received by the computer system 706. The brain modelling engine 806 can take some action (e.g., refer to step E in FIG. 1) in response to receiving the user input (e.g., refer to step D in FIG. 1). That action can include, for example, simulating removal of one or more nodes in the patient's brain. The GUI generation engine 808 can generate updated GUI displays based on the actions taken by the brain modelling engine 806 (e.g., refer to step F in FIG. 1). The GUI generation engine 808 can then transmit the updated GUI displays to the user device 104 to be outputted to the medical professional.

Sometimes, one or more of the components of the computer system 706, such as the brain modelling engine 806 and the GUI generation engine 808 can be part of one or more different systems. For example, the brain modelling engine 806 can be part of a software application program that can be loaded and/or executed at another device, such as the user device 104 and/or the medical imaging device 706. As another example, the GUI generation engine 808 can be part of a software application program that is executed at the user device 104 and the brain modelling engine 806 can be executed at the computer system 706 or another remote computing system, server, or cloud-based server or system.

The user device 104 can include processor(s) 814, input device(s) 816, output device(s) 818, application interface 820, and communication interface 822. The processor(s) 814 can be configured to perform one or more operations described herein. Although not depicted, the user device 104 can also include at least one memory unit, which may have semiconductor random access memory (RAM) and semiconductor read only memory (ROM).

The input device(s) 816 and output device(s) 818 can include one or more of an audio-video interface that couples to a video display, speakers, and/or a microphone, keyboard, mouse, scanner, camera, touch screen display, other display screen(s) (e.g., LCDs), joystick, and/or other human interface device. The input device(s) 816 can be configured to receive user input from the medical professional or other user. The output device(s) 818 can be configured to output the model of the patient's brain and/or actions taken by the computer system 706 in response to the user input. The output device(s) 818 can present a variety of GUI displays and information to the medical professional, where such displays and information are generated by the computer system 706. The output device(s) 818 can also output information that is received or otherwise generated by the medical imaging device 710.

The application interface 820 can be executable software or another program that is deployed at the user device 104. The GUIs generated by the computer system 706 can be displayed or otherwise outputted via the application interface 820. In some implementations, the application interface 820 can be executed at a browser of the user device 104. The medical professional can then access and view the GUIs via the Internet or other connection. Sometimes, the application interface 820 can be executed as a software module/program/product at the user device 104. The application interface 820 can provide the interactive GUIs to the medical professional and receive input from the medical professional (e.g., refer to FIG. 3).

The communication interfaces 804 and 822 can be configured to provide communication between and amongst the components described herein. For example, a modem can be integrated therein.

Figure 9:
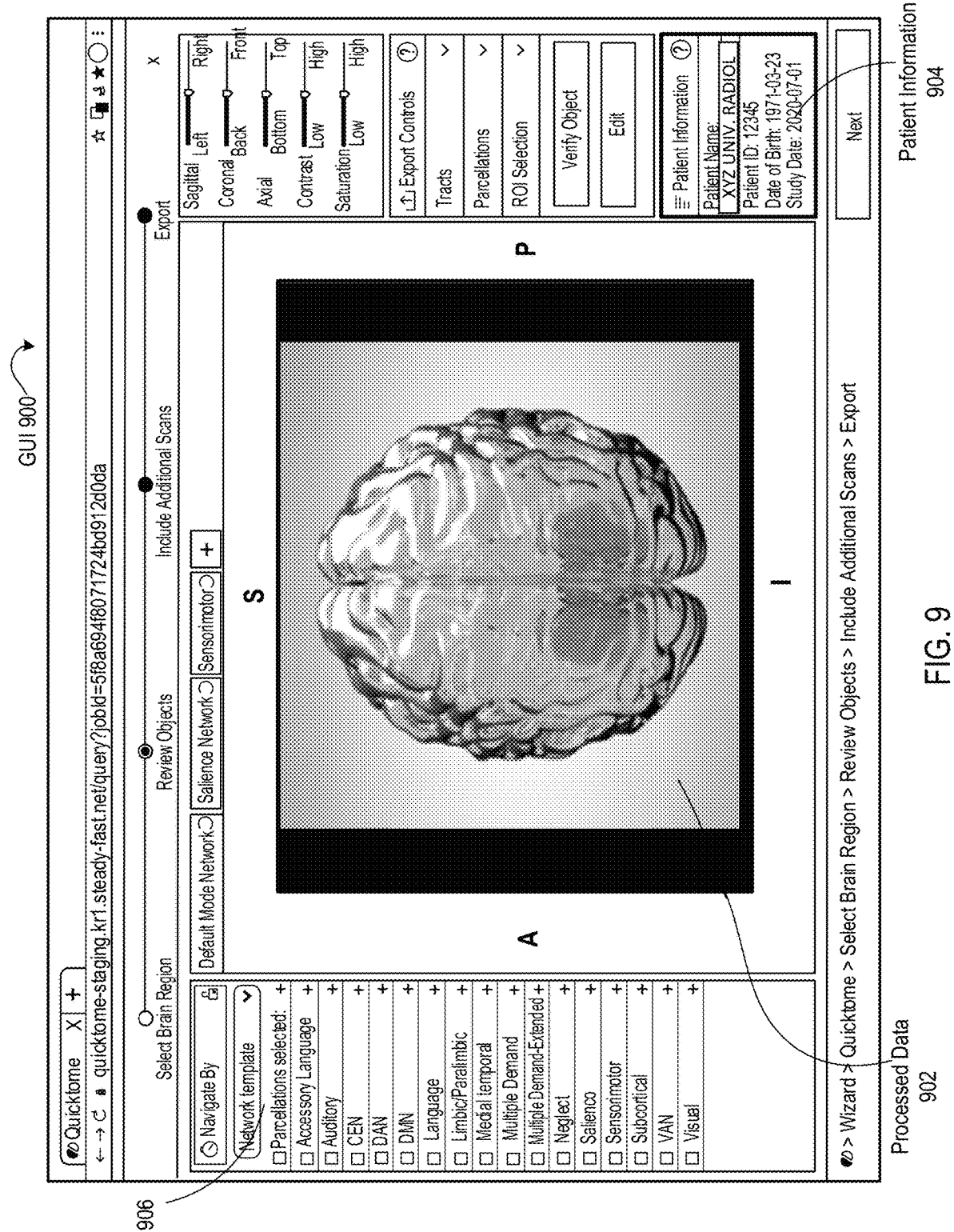
FIG. 9 illustrates a user-interactive GUI of the particular brain.

FIG. 9 illustrates a user-interactive GUI 900 of the particular brain. The GUI 900 can be outputted at the user device 104 described herein. The GUI 900 outputs processed medical imaging data that is received of the particular brain. For example, the GUI 900 can include processed data 902, patient information 904, and selectable options 906. The processed data 902 can include the particular brain as it is modeled on a representation of a brain. For example, the processed data 902 can include a 3D representation of the particular brain, such as the particular brain overlaying a glass brain. The processed data 902 also may not include other information that can appear in imaging data, such as patient information or other PHI. The PHI that corresponds to the processed data 902 can optionally be outputted in the patient information 904.

The GUI 900 can provide a brain navigation system that is configured to display visual representations of an interior of the particular brain for clinical analysis and medical intervention, as well as visual representation of physiology of specific portions or objects of the brain (e.g. tracts, hubs, or parcels of the brain). Such visual representations can reveal internal structures hidden by the skin and bones, and can be used to diagnose and treat various different diseases.

The medical professional can use the selectable options 906 to specify particular actions (e.g. by making selections in the GUI 900 presented at the user device 104) that the medical professional would like to take with regards to the processed data 902. The medical professional can also choose options to export the processed data within an IT network of the hospital or other medical setting where the medical professional works. The medical professional can save the exported data (e.g., in the data store 108 in FIG. 1), which can be used in future research and analysis.

The GUI 900 presents only some options that may be presented to the medical professional with regards to the processed data 902. One or more other options are also possible and can be presented in the GUI 900 and/or in additional GUIs that are outputted at the user device 104.

Moreover, as described herein, the GUI 900 can be part of a specialized computing system in the hospital IT infrastructure. Sometimes, the GUI 900 can also be accessible via a web browser. The GUI 900 may be configured—e.g. by authentication mechanisms such as login using username and/or password, biometric detection, and/or the like—to be used by only authorized individuals, such as clinicians (e.g. doctors, nurses, clinical staff, or the like), other medical professionals, or other authorized users (e.g. network administrator, technical staff, or the like) at the hospital or other medical setting. In some implementations, the GUI 900 can also be in communication with or otherwise linked to one or more external devices, such as remote computers, that can be used to facilitate brain surgery or other medical procedures.

Although a brain image is useful for a medical professional, the medical professional can benefit more if they have additional information about components of the brain that is imaged. This additional information can be advantageous for the medical professional to make more informed decisions with regard to diagnosis, treatment, and medical procedures. Accordingly, as shown in FIG. 3, the GUI 900 can provide the medical professional with tools (e.g., such as the selectable options 906) that allow the medical professional to interact with the modelled version of the particular brain. The medical professional can provide input for selecting portions of the processed data 902. The selected portions can be objects—e.g. brain tracts and/or brain parcels that the medical professional desires to see more information about, remove from the brain in a simulated procedure, or otherwise review and analyze. Accordingly, the medical professional can specify particular portions of the brain to analyze. The medical professional may also desire to identify and specify, on the GUI 900, particular objects on several features, such as local properties of brain tissue, long-range connectivity patterns, structural markers, functional markers, and/or the like. The disclosed technology therefore can provide the medical professional with a more comprehensive, interactive, and user friendly interface for making determinations about a particular patient's brain condition(s).

Figure 10:
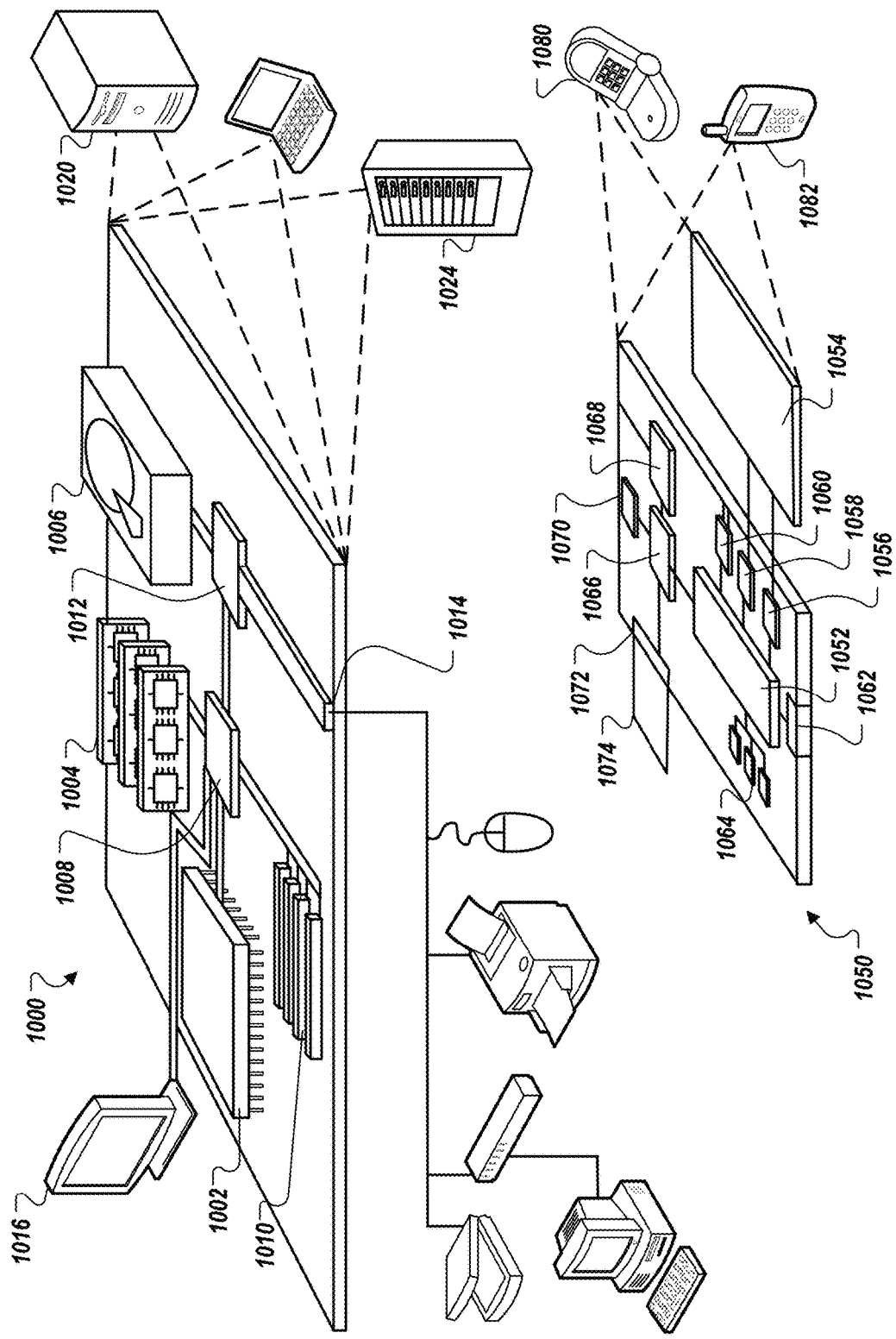
FIG. 10 shows an example of a computing device and an example of a mobile computing device.

FIG. 10 shows an example of a computing device 1000 and an example of a mobile computing device that can be used to implement the techniques described here. The computing device 1000 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1000 includes a processor 1002, a memory 1004, a storage device 1006, a high-speed interface 1008 connecting to the memory 1004 and multiple high-speed expansion ports 1010, and a low-speed interface 1012 connecting to a low-speed expansion port 1014 and the storage device 1006. Each of the processor 1002, the memory 1004, the storage device 1006, the high-speed interface 1008, the high-speed expansion ports 1010, and the low-speed interface 1012, are interconnected using various busses, and can be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as a display 1016 coupled to the high-speed interface 1008. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1004 stores information within the computing device 1000. In some implementations, the memory 1004 is a volatile memory unit or units. In some implementations, the memory 1004 is a non-volatile memory unit or units. The memory 1004 can also be another form of computer-readable medium, such as a magnetic or optical disk.

The storage device 1006 is capable of providing mass storage for the computing device 1000. In some implementations, the storage device 1006 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1004, the storage device 1006, or memory on the processor 1002.

The high-speed interface 1008 manages bandwidth-intensive operations for the computing device 1000, while the low-speed interface 1012 manages lower bandwidth-intensive operations. Such allocation of functions is exemplary only. In some implementations, the high-speed interface 1008 is coupled to the memory 1004, the display 1016 (e.g., through a graphics processor or accelerator), and to the high-speed expansion ports 1010, which can accept various expansion cards (not shown). In the implementation, the low-speed interface 1012 is coupled to the storage device 1006 and the low-speed expansion port 1014. The low-speed expansion port 1014, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1000 can be implemented in a number of different forms, as shown in the figure. For example, it can be implemented as a standard server 1020, or multiple times in a group of such servers. In addition, it can be implemented in a personal computer such as a laptop computer 1022. It can also be implemented as part of a rack server system 1024. Alternatively, components from the computing device 1000 can be combined with other components in a mobile device (not shown), such as a mobile computing device 1050. Each of such devices can contain one or more of the computing device 1000 and the mobile computing device 1050, and an entire system can be made up of multiple computing devices communicating with each other.

The mobile computing device 1050 includes a processor 1052, a memory 1064, an input/output device such as a display 1054, a communication interface 1066, and a transceiver 1068, among other components. The mobile computing device 1050 can also be provided with a storage device, such as a micro-drive or other device, to provide additional storage. Each of the processor 1052, the memory 1064, the display 1054, the communication interface 1066, and the transceiver 1068, are interconnected using various buses, and several of the components can be mounted on a common motherboard or in other manners as appropriate.

The processor 1052 can execute instructions within the mobile computing device 1050, including instructions stored in the memory 1064. The processor 1052 can be implemented as a chipset of chips that include separate and multiple analog and digital processors. The processor 1052 can provide, for example, for coordination of the other components of the mobile computing device 1050, such as control of user interfaces, applications run by the mobile computing device 1050, and wireless communication by the mobile computing device 1050.

The processor 1052 can communicate with a user through a control interface 1058 and a display interface 1056 coupled to the display 1054. The display 1054 can be, for example, a TFT (Thin-Film-Transistor Liquid Crystal Display) display or an OLED (Organic Light Emitting Diode) display, or other appropriate display technology. The display interface 1056 can comprise appropriate circuitry for driving the display 1054 to present graphical and other information to a user. The control interface 1058 can receive commands from a user and convert them for submission to the processor 1052. In addition, an external interface 1062 can provide communication with the processor 1052, so as to enable near area communication of the mobile computing device 1050 with other devices. The external interface 1062 can provide, for example, for wired communication in some implementations, or for wireless communication in other implementations, and multiple interfaces can also be used.

The memory 1064 stores information within the mobile computing device 1050. The memory 1064 can be implemented as one or more of a computer-readable medium or media, a volatile memory unit or units, or a non-volatile memory unit or units. An expansion memory 1074 can also be provided and connected to the mobile computing device 1050 through an expansion interface 1072, which can include, for example, a SIMM (Single In Line Memory Module) card interface. The expansion memory 1074 can provide extra storage space for the mobile computing device 1050, or can also store applications or other information for the mobile computing device 1050. Specifically, the expansion memory 1074 can include instructions to carry out or supplement the processes described above, and can include secure information also. Thus, for example, the expansion memory 1074 can be provide as a security module for the mobile computing device 1050, and can be programmed with instructions that permit secure use of the mobile computing device 1050. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1064, the expansion memory 1074, or memory on the processor 1052. In some implementations, the computer program product can be received in a propagated signal, for example, over the transceiver 1068 or the external interface 1062.

The mobile computing device 1050 can communicate wirelessly through the communication interface 1066, which can include digital signal processing circuitry where necessary. The communication interface 1066 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1068 using a radio-frequency. In addition, short-range communication can occur, such as using a Bluetooth, WiFi, or other such transceiver (not shown). In addition, a GPS (Global Positioning System) receiver module 1070 can provide additional navigation- and location-related wireless data to the mobile computing device 1050, which can be used as appropriate by applications running on the mobile computing device 1050.

The mobile computing device 1050 can also communicate audibly using an audio codec 1060, which can receive spoken information from a user and convert it to usable digital information. The audio codec 1060 can likewise generate audible sound for a user, such as through a speaker, e.g., in a handset of the mobile computing device 1050. Such sound can include sound from voice telephone calls, can include recorded sound (e.g., voice messages, music files, etc.) and can also include sound generated by applications operating on the mobile computing device 1050.

The mobile computing device 1050 can be implemented in a number of different forms, as shown in the figure. For example, it can be implemented as a cellular telephone 1080. It can also be implemented as part of a smart-phone 1082, personal digital assistant, or other similar mobile device.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
receiving a selection of a medical condition;
obtaining data identifying a plurality of brain parcels that are predicted to be relevant to the medical condition;
receiving fMRI data for a brain of a subject;
processing the fMRI data for the brain of the subject to determine a respective activation score for each of the plurality of brain parcels that are predicted to be relevant to the medical condition;
determining, for each of the plurality of brain parcels that are predicted to be relevant to the medical condition, a relative activation score for the brain parcel based on: (i) the activation score for the brain parcel in the subject, and (ii) a distribution of activation scores for the brain parcel across a population of subjects;
providing, to a user device of a user, the relative activation scores for the plurality of brain parcels that are predicted to be relevant to the medical condition as explainability data that explains the medical condition in the subject; and
taking an action based on the relative activation scores.

2. The method of claim 1, wherein taking an action based on the relative activation scores comprises:

after providing the relative activation scores to the user device of the user, receiving selection data from the user that selects one or more of the plurality of brain parcels that are predicted to be relevant to the medical condition; and
taking the action in response to receiving the selection data from the user.

3. The method of claim 2, wherein taking the action in response to receiving the selection data from the user comprises:
obtaining, for each selected brain parcel, respective anatomical data that defines a volumetric region in the brain of the subject that corresponds to the selected parcel; and
providing, for display on the user device, a visual representation of the anatomical data for the selected brain parcels as part of a three-dimensional model of the brain of the subject.

4. The method of claim 2, wherein taking the action in response to receiving the selection data from the user comprises:
exporting data identifying the selected brain parcels.

5. The method of claim 1, wherein for each of the plurality of brain parcels that are predicted to be relevant to the medical condition, determining the relative activation score for the brain parcel comprises:
determining the relative activation score for the brain parcel based on a ratio of: (i) the activation score for the brain parcel in the subject, and (ii) a measure of central tendency of the distribution of activation scores for the brain parcel across the population of subjects.

6. The method of claim 5, wherein the measure of central tendency is a mean or a median.

7. The method of claim 1, wherein the plurality of brain parcels that are predicted to be relevant to the medical condition have been identified by operations comprising:
training a machine learning model to process an input derived from functional magnetic resonance imaging (fMRI) data for a brain of an input subject to predict whether the input subject has the medical condition;
identifying the plurality of brain parcels that are predicted to be relevant to the medical condition using the machine learning model.

8. The method of claim 7, wherein identifying the plurality of brain parcels that are predicted to be relevant to the medical condition using the machine learning model comprises:
determining, for each brain parcel in a parcel atlas, a respective importance score for the brain parcel that measures an impact of the brain parcel on predictions generated by the machine learning model; and
identifying the plurality of brain parcels that are predicted to be relevant to the medical condition using the importance scores for the brain parcels in the parcel atlas.

9. The method of claim 8, wherein identifying the plurality of brain parcels that are predicted to be relevant to the medical condition using the importance scores for the brain parcels in the parcel atlas comprises:
identifying each brain parcel in the parcel atlas having an importance score that satisfies a predefined threshold as being relevant to the medical condition.

10. The method of claim 8, wherein identifying the plurality of brain parcels that are predicted to be relevant to the medical condition using the importance scores for the brain parcels in the parcel atlas comprises:

identifying a predefined number of brain parcels that are associated with the highest importance scores from the brain parcels in the parcel atlas as being relevant to the medical condition.

11. The method of claim 7, wherein training a machine learning model to process an input derived from fMRI data for a brain of an input subject to predict whether the input subject has the medical condition comprises:
training the machine learning model on a set of training data comprising a plurality of training examples, wherein each training example includes: (i) a training input derived from fMRI data for a brain of a training subject, and (ii) a label defining whether the training subject has the medical condition.

12. The method of claim 7, wherein the machine learning model is configured to process an input that comprises a functional connectivity matrix derived from fMRI data for the brain of the input subject.

13. The method of claim 7, wherein the machine learning model is configured to generate an output that defines a predicted likelihood that the input subject has the medical condition.

14. The method of claim 7, wherein the machine learning model comprises a neural network model.

15. The method of claim 1, wherein the plurality of brain parcels that are predicted to be relevant to the medical condition are a proper subset of a set of parcels that collectively define a parcel atlas.

16. The method of claim 15, wherein the plurality of brain parcels that are predicted to be relevant to the medical condition comprise fewer than 5% of the set of parcels that collectively define the parcel atlas.

17. The method of claim 1, wherein the medical condition is a psychiatric condition or a behavioral symptom of a psychiatric condition.

18. The method of claim 1, wherein for each of the plurality of brain parcels that are predicted to be relevant to the medical condition, the activation score for the brain parcel characterizes blood flow in the brain parcel in the brain of the subject.

19. A system comprising:
one or more computers; and
one or more storage devices communicatively coupled to the one or more computers, wherein the one or more storage devices store instructions that, when executed by the one or more computers, cause the one or more computers to perform operations comprising:
receiving a selection of a medical condition;
obtaining data identifying a plurality of brain parcels that are predicted to be relevant to the medical condition;
receiving fMRI data for a brain of a subject;
processing the fMRI data for the brain of the subject to determine a respective activation score for each of the plurality of brain parcels that are predicted to be relevant to the medical condition;
determining, for each of the plurality of brain parcels that are predicted to be relevant to the medical condition, a relative activation score for the brain parcel based on: (i) the activation score for the brain parcel in the subject, and (ii) a distribution of activation scores for the brain parcel across a population of subjects;
providing, to a user device of a user, the relative activation scores for the plurality of brain parcels that are predicted to be relevant to the medical condition as explainability data that explains the medical condition in the subject; and
taking an action based on the relative activation scores.

20. One or more non-transitory computer storage media storing instructions that when executed by one or more computers cause the one or more computers to perform operations comprising:
receiving a selection of a medical condition;
obtaining data identifying a plurality of brain parcels that are predicted to be relevant to the medical condition;
receiving fMRI data for a brain of a subject;
processing the fMRI data for the brain of the subject to determine a respective activation score for each of the plurality of brain parcels that are predicted to be relevant to the medical condition;
determining, for each of the plurality of brain parcels that are predicted to be relevant to the medical condition, a relative activation score for the brain parcel based on: (i) the activation score for the brain parcel in the subject, and (ii) a distribution of activation scores for the brain parcel across a population of subjects;
providing, to a user device of a user, the relative activation scores for the plurality of brain parcels that are predicted to be relevant to the medical condition as explainability data that explains the medical condition in the subject; and
taking an action based on the relative activation scores.

* * * * *